(12) United States Patent
Hashimoto

(10) Patent No.: US 10,323,044 B2
(45) Date of Patent: Jun. 18, 2019

(54) CRYSTAL OF IMIDAZO-OXAZINE, PHARMACEUTICAL COMPOSITION CONTAINING SAID CRYSTAL, AND METHOD FOR PRODUCING SAID CRYSTAL

(71) Applicant: TAIHO PHARMACEUTICAL CO., LTD., Chiyoda-ku, Tokyo (JP)

(72) Inventor: Masaya Hashimoto, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 15/553,286

(22) PCT Filed: Feb. 26, 2016

(86) PCT No.: PCT/JP2016/055752
§ 371 (c)(1),
(2) Date: Aug. 24, 2017

(87) PCT Pub. No.: WO2016/136928
PCT Pub. Date: Sep. 1, 2016

(65) Prior Publication Data
US 2018/0030067 A1    Feb. 1, 2018

(30) Foreign Application Priority Data
Feb. 27, 2015   (JP) ................................. 2015-038435

(51) Int. Cl.
*C07D 498/14* (2006.01)

(52) U.S. Cl.
CPC ........ *C07D 498/14* (2013.01); *C07B 2200/13* (2013.01)

(58) Field of Classification Search
CPC .................................................... C07D 498/14
USPC ......................................................... 544/95
See application file for complete search history.

(56) References Cited

U.S. PATENT DOCUMENTS

| | | | |
|---|---|---|---|
| 8,772,283 B2 | 7/2014 | Nakamura et al. | |
| 9,375,434 B2 | 6/2016 | Ichikawa et al. | |
| 2009/0023149 A1 | 1/2009 | Knudsen | |
| 2010/0069629 A1 | 3/2010 | Shimma et al. | |
| 2011/0319354 A1 | 12/2011 | Layton et al. | |
| 2014/0005185 A1 | 1/2014 | Nakamura et al. | |

FOREIGN PATENT DOCUMENTS

| | | |
|---|---|---|
| CN | 1942465 A | 4/2007 |
| JP | S57-212188 A | 12/1982 |
| JP | 2010-535847 A | 11/2010 |
| JP | 2015-503601 A | 2/2015 |
| RU | 2448109 C2 | 4/2012 |
| WO | 2005/100344 A1 | 10/2005 |
| WO | 2008070016 A2 | 6/2008 |
| WO | 2009/021990 A1 | 2/2009 |
| WO | 2009/148916 A1 | 12/2009 |
| WO | 2010/087497 A1 | 8/2010 |
| WO | 2012/007345 A2 | 1/2012 |
| WO | 2012/137870 A1 | 10/2012 |
| WO | WO 2012137870 A1 * | 10/2012 ........... C07D 498/04 |
| WO | 2013/104610 A1 | 7/2013 |

OTHER PUBLICATIONS

Kettle et al., "Diverse Heterocyclic Scaffolds as Allosteric Inhibitors of AKT", Journal of Medical Chemistry, 2012, vol. 55, No. 3, pp. 1261-1273.
"Physico-Chemical Studies on the Molecular Details of Drug Crystals", Pharm Tech Japan, 2002, vol. 18, No. 10. pp. 81-96.
Yozai Handbook, 6th print, 1985, pp. 47-51.
Jikken Guidebook, 3rd print, 1992, pp. 130-131.
Tanno et al., "Serine/Thereonine Kinase AKT is Frequently Activated in Human Bile Duct Cancer and is associated with Increased Radioresistance", Cancer Research, 64, pp. 3486-3490, 2004.
Uegaki et al., "PTEN—positive and phosphorylated-Akt-negative expression is a predictor of survival for patients with advanced endometrial carcinoma", Oncol. Rep., 2005, 14(2), pp. 389-92 (Abstract only).
Valkov et al., "The prognositic impact of Akt isoforms, PI3K and PTEN related to female steroid hormone receptors in soft tissue sarcomas", Journal of Translational Medicine, 2011, 9, 200, 12 pages.
Yoshioka et al., "The activation of Akt during preoperative chemotherapy for esophageal cancer correlates with poor prognosis", Oncology Reports, 2008, 19, pp. 1099-1107.
Yuan et al., "Frequent activation of AKT2 and induction of apoptosis by inhibition of phosphoinositide-3-OH kinase/Akt pathway in humna overian cancer", Oncogene, 2000, 19, pp. 2324-2330.
Zhang et al, "Pl3k/Akt signaling in osteosarcoma", Clinica Chimica Acta, 444, 2015, pp. 182-192.
Zhou et al, "Activation of the Akt/Mammalian Target of Rapamycin/ 4E-BP1 Pathway by ErbB2 Overexpression Predicts Tumor Progression in Breast Cancer", Clinical Cancer Research, vol. 10, 2014, pp. 6779-6788.
Hirai et al., "MK-2206, an Allosteric Akt Inhibitor, Enhances Antitumor Efficacy by Standard Chemotherapeutic Agents pr Molecular Targeted Drugs in vitro and in vivo", Molecular Cancer Therapeutics, 2010, vol. 9, No. 7, pp. 1956-1967.

(Continued)

*Primary Examiner* — Kahsay Habte
(74) *Attorney, Agent, or Firm* — Rothwell, Figg, Ernst & Manbeck, P.C.

(57) ABSTRACT

An object of the present invention is to provide a crystal of trans-3-amino-1-methyl-3-(4-(3-phenyl-5H-imidazo[1,2-c]pyrido[3,4-e][1,3]oxazin-2-yl)phenylcyclobutanol having excellent stability and favorable characteristics in terms of its production and formulation into drugs. The present invention provides a crystal of trans-3-amino-1-methyl-3-(4-(3-phenyl-5H-imidazo[1,2-c]pyrido[3,4-e][1,3]oxazin-2-yl)phenylcyclobutanol having characteristic peaks of diffraction angle (2θ±0.1°) at 7.7°, 9.5°, 10.3°, 12.3°, 14.5°, 15.6°, 16.3°, 17.8°, 18.3°, 19.3°, 20.9°, 22.8°, 24.2°, 25.7°, 26.8°, 27.7°, 29.0° and 30.1° in a powder X-ray diffraction spectrum.

6 Claims, 5 Drawing Sheets

(56) References Cited

OTHER PUBLICATIONS

Lopiccolo et al., "Targeting the PI3K/Akt/mTOR pathway:Effective combinations and clinical considerations", Drug Resistance Updates, 2008, vol. 11, pp. 32-50.
Markman et al., "Status of PI3K inhibition and biomarker development in cancer therapeutics", Annals of Oncology, 2010, vol. 21, No. 4, pp. 683-691.
Liy et al., "Allosteric inhibitors of Akt1 and Akt2: Discovery of [1,2,4]triazolo[3,44]11,61naphthyridines with potent and balanced activity", Bioorganic & Medicinal Chemistry Letters, vol. 19, No. 3, 2009, pp. 834-836.
AKT Wikipedia Entry, Protein Kinase B, edited Jan. 22, 2018, 6 pages.
Hers et al., "Akt signalling in health and disease", Cellular Signalling, vol. 23, 2011pp. 1515-1527.
Garrido-Laguna et al., "Integrated preclinical and clinical development of mTOR inhibitors in pancreatic cancer", British Journal of Cancer, 2010, 103, pp. 649-655.
Venkatesh et al., "Role of Development Scientist in Compound Lead Selection and Optimization", Journal of Pharmaceutical Science, vol. 89, No. 2, 2000, pp. 145-54.
Dienstmann et al., "Picking the Point of Inhibition: A Comparative Review of PI3K/Akt/mTOR Pathway Inhibitors", Molecular Cancer Therapeutics, 13(5), pp. 1021-1031, 2014.
Freshney, "Culture of Animal Cells", A Manual of Basic Technique, 1983, p. 4.
Mahesh et al., "Analogs of cannabinoids: sythesis of some 7H-indolo-, 5H-imidazolo, 7H-benzimidazolo [1,2-c] [1,3] benzoxazines-novel ring systems", Canadian Journal of Chemistry, 1985, vol. 63, No. 3, pp. 632-635.
Manning et al., "AKT/PKB Signaling: Navigating Downstream", Cell, 2007, vol. 129, No. 7, pp. 1261-1274.
Qiad et al., "Metastasis and AKT activation", Cell Cycle, 2008, vol. 7, No. 19, pp. 2991-2996.
Staal, "Molecular cloning of the akt oncogene and its human homologues AKT1 and AKT2: Amplification of AKT1 in a primary human gastric adenocarcinoma", Proceedings of the National Academy of Sciences of the United States of America, 1987, vol. 84, pp. 5034-5037.
Brodbeck et al., "A Human Protein Kinase bv with Regulatry Phosphorylation Sites in the Activation Loop and in the C-terminal Hydrophobic Domain", The Journal of Biological Chemistry, 1999, vol. 274, No. 14, pp. 9133-9136.
Schieid et al., "unravelling the activation mechanisms of protein kinase B/Akt", FEBS Letters, 2003, vol. 546, pp. 108-112.
Liu et al, "Targeting the phosphoinositide 3-kinase pathway in cancer", Nature Reviews Drug Discovery, 2009, vol. 8, pp. 627-644.
LoPiccolo et al., "Targeting Akt in cancer therapy", Anti-Cancer Drugs, 2007, vol. 18, No. 8, pp. 861-874.
Wen et al., "Current clinical development of PI3K pathway inhibitors in glioblastoma", Neuro-Oncology, 14(7): 819-829, 2012.
Kwei et al., "Modulators of Sensitivity and Resistance to Inhibition of PI3K Identified in a Pharmacogenomic Screen of the NCI-60 Human Tumor Cell Line Collection", PLOS ONE,2012, vol. 7, No. 9,e46518, 13 pages.
Noh et al., "Determinants of Rapamycin Sensitivity in Breast Cancer Cells", Clinical Cancer Research, 2004, vol. 10, pp. 1013-1023.
O'Reilly and McSheehy, "Biomarker Development for the Clinical Activity of the mTOR Inhibitor Everolimus (RAD001): Processes, Limitations, and Further Proposals", Translational Oncology, 2010, vol. 3, No. 2, pp. 65-79.
3Boller et al., "Targeting PI3KC2β Impairs Proliferation and Survival in Acute Leukemia, Brain Tumours and Neuroendocrine Tumours", Anti Cancer Research, 2012, pp. 3015-3028.
Knobbe et al., "Genetic Alterations and Aberrant Expression of Genes Related to the Phosphatidyl-Inositol-3'-Kinase/Protein Kinase B (Akt) Signal Transduction Pathway in Glioblastomas" Brain Pathology, vol. 13, No. 4, 2003, pp. 507-518.

Dan et al., "Correlating Phosphatidylinositol 3-Kinase Inhibitos Efficacy with Signaling Pathway Status: In silico and Biological Ecaluations",Cancer Research, vol. 70, No. 12, 2010, pp. 4982-4994.
Sadeghi et al., "Targeting the PI3K pathway for cancer therapy", Future Medicinal Chemistry, vol. 4, No. 9, 2012, pp. 1153-1169.
Yunokawa et al., "Efficacy of everolimus, a novel mTOR inhibitor, against basal-like triple-negative breast cancer cells", Cancer Science, 2012, vol. 103, No. 9, pp. 1665-1671.
Shi et al., "Enhanced Sensitivity of Multiple Myeloma Cells Containing PTEN Mutations to CCI-779", Cancer Research, 62, 2002, pp. 5027-5034.
Arcaro et al., "Two distinct phosphoinositide 3-kinases mediate polypeptide growth factor-stimulated PKB activation", The EMBO Journal, 2002, vol. 21, No. 19, pp. 5097-5108.
De Roock et al., "KRAS, BRAF, PIK3CA, and PTEN mutations: implications ofr targeted therapies in metastatic colorectal cancer", Lancet Oncology, 2011, vol. 12, pp. 594-603.
Domin et al., "The Class II Phosphoinositide 3-Kinase PI3KC2β Regulates Cell migration by a PtdIns(3)p. Dependent Mechanism" Journal of Cellular Physiology, 2005, vol. 205, No. 3, pp.452-462.
Engelman, "Targeting PI3K signalling in cancer, opportunities, challenges and limitations", Nature Reviews Cancer, 2009, vol. 9, pp. 550-562.
La Thangue et al., "Predictive biomarkers: aparadigm shift thowards personalized caner medicine", Nature Reviews Clinical Oncology, 2011, vol. 8, pp. 587-596.
Liu et al., "Phosphatidylinositol 3-Kinase-C2β Inhibits Cisplatin-mediated Apoptosis via the Akt Pathway in Oesophageal Squamous Cell Carcinoma", The Journal of International Medical Research, 2011, vol.39, No. 4, pp. 1319-1332.
Traer et al., "Are class II phosphoinositide 3-kinases potential targets for anticancer therapies?"Bulletin du Cancer, 2006, vol. 93, No. 5, pp. 53-58.
Vivanco et al., "The phosphatidylinositol 3-Kinase-Akt pathway in human cancer", Nature Reviews Cancer, 2002, vol.2, pp. 489-501.
Wang et al., "Abstract 20: PHLDA12 contribute to tumor suppression in breast and lung cancer as downstream targets of oncogenic HER2 signalling", Cancer Research, 2012, vol. 72, Issue 8, Supplement 1.
Bertelsen et al., "Molecular analysis of the PI3K-Akt pathway in uterine cervical neoplasia: Frequent PIK3CA amplification and Akt phosphorylation", INT. J. Cancer, 118, pp. 1877-1883, 2006.
Boyault et al., "Transcriptome Classification of HCC is Related to Gene Alterations and to New Therapeutic Targets", Hepatology, 2007, 45, pp. 42-52.
Catasus et al., "Expression profiling of 22 genes involved in the PI3K-Akt pathway identified two subgroups of highgrade endometrial carcinomas with different moleculart alterations", Modem Pathlogy, 2010, 23, pp. 694-702.
Chakravarti et al., "The Prognostic Significance of Phosphatidylinositol 3-Kinase Pathway Activation in Human Gliomas", Journal of Clinical Oncology, vol. 22, No. 10, 2004, pp. 1926-1933.
Chen et al., "Involvement of PI3K/PTEN/AKT/mTOR pathway in invasion and metastasis in hepatocellular carcinoma: Association with MMP-9", Hepatology Research, 2009, 39: pp. 177-186.
Fillmore et al., "Expression of Akt (protein kinase B) and its isoforms in malignant lymphomas" Leuk Lymphoma, 2005, 46 (12), pp. 1765-73 (Abstract only).
Hagar et al., "p-AKT overexpression in primary renal cell carcinomas and their metastases", Clin Exp Metastasis, 2010, 27, pp. 611-617.
Hasselblom et al., High immunohistochemical expression of p-AKT predicts inferior survival in patients with diffuse large B-cell lymphoma treated with immunochemotherapy, British Journal of Haematology, 2010, 149, pp. 560-568.
Hideshima et al., "Perifosine, an oral bioactive novel alkyphospholipid, inhibits Alt and induces in vitro and in vivo cytotoxicity in human multiple myeloma cells", Blood, 2006, 107, pp. 4053-4062.
Jendrossek et al., "Analysis of complex protein kinase B signalling pathways in human prostate cancer sample", BJU International, 2008, 102, pp. 371-382.

(56) References Cited

OTHER PUBLICATIONS

Knowles et al., "Phospatidilinositol 3-kinase (PI3K) pathway activation in bladder cancer", Cancer Metastasis Rev., 2009, 28, pp. 305-316.

Korkolopoulou et al., "A comprehensive immunohistochemical and molecular approach to the PI3K/AKT/mTOR (phosphoinositide 3-kinase/v-akt murine thymona viral oncogene/mammalian target of rapamycin) pathway in bladder urothelial carcinoma", BJU International, 2012, 110, E1237-E1248.

Min et al., "Constitutive phosphorylation of AKT/PKB protein in acute myeloid leukemia: its significance as a prognostic variable", Luekemia, 2003, 17, pp. 995-997.

Murakami et al., "Expression of phosphorylated Akt(pAkt) in gastric carcinoma predicts prognosis and efficacy of chemotherapy", Gastric Cancer, 2007, 10, pp. 45-51.

Niakai et al., "KIT (c-kit oncogene product) pathway is consititutively activated in human testicular germ cell tumors", Biochemical and Biophysical Research Communications, 337, 2005, pp. 289-296.

Oh et al., "Clinicopathologica correlations of mTOR and pAkt expression in non-small cell lung cancer", Virchows Arch, 2012, 460, pp. 601-609.

Pignochino et al., "Targeting EGFR/HER2 pathways enhances the antiproliferative effect of gemcitabine in biliary track and gallbladder carcinomas", BMC Cancer, 2010, 10, 631, pp. 1-14.

Pedrero et al., "Frequent genetic and biochemical alterations of the PI 3-K/AKT/PTEN pathway in head and neck squamous cell carcinoma", Int. J. Cancer, 114, pp. 242-248, 2005.

Roy et al., "AKT proto-oncogene overexpression in an early event during sporadic colon carcinogenesis", Carcinogeneis, vol. 23, No. 1, pp. 201-205, 2002.

Sagatys et al., "Activation of the serine/threonine protein kinase Akt during the progression of Barrett neoplasia", Human Pathology, 2007, 38, pp. 1526-1531.

Schlieman et al., "Incidencem mechanism and prognostic value of activated AKT in pancreas cancer", British Journal of Cancer, 2003, 89, pp. 2110-2115.

Stahl et al., Deregulated Akt3 Activity Promotes Develepment of Malignant Melanoma, Cancer Research, 64, 2004, pp. 7002-7010.

Sun et al., "AKT1PLBa Kinase is Frequently Elevated in Human Cancers and its Constitutive Activation is Required for Oncogenic Transformation in NIH3T3 Cells", American Journal of Pathology, vol. 159, No. 2, 2001, pp. 431-437.

Anderson, "Practical Process Research & Development, Chapter 11, Tools for Purifying the Product: Column chromatography, Crystallization and Reslurrying", 2000, Practical Process Research & Development, Jan. 1, 2000, pp. 223-224.

Byrn et al., "Pharmaceutical Solids: A Strategic Approach to Regulatory Considerations", Pharmaceutical Research, vol. 12, No. 7, 1995, pp. 945-954.

extended European search report for the corresponding EP patent application No. 16755672.9 dated Jul. 13, 2018, 7 pages.

Belikov v.g., "Relationship Between the Structure of Substance Molecules and Their Action on the Organism", Pharmaceutical Chemistry, M., Vishaya Shkola, 1993, pp. 43-47 (with translation).

Kharkevich D.A. Pharmacology: Textbook. M.: Geotar Media, 2006.—736 pages, pp. 66-71 (with translation).

Office Action for the related RU patent application No. 2015103151, dated Jun. 6, 2016, 10 pages. (with translation).

Yang Lu et al., "Polymorphic Drugs", People's Health Publishing House, 1st edition, 2009, pp. 5-13 (Partial Translation).

Office Action for the corresponding CN Patent Application No. 201680018450.0, dated Nov. 27, 2018, 15 pages.

\* cited by examiner

US 10,323,044 B2

CRYSTAL OF IMIDAZO-OXAZINE, PHARMACEUTICAL COMPOSITION CONTAINING SAID CRYSTAL, AND METHOD FOR PRODUCING SAID CRYSTAL

CROSS REFERENCE TO RELATED APPLICATION

This application is a 35 U.S.C. 371 National Phase Entry Application from PCT/JP2016/055752, filed Feb. 26, 2016, which claims the benefit of Japanese Patent Application No. 2015-038435 filed on Feb. 27, 2015, the disclosure of which is incorporated herein in its entirety by reference.

TECHNICAL FIELD

The present invention relates to a novel crystal of an imidazooxazine compound with excellent storage stability useful as an antitumor agent; a pharmaceutical composition comprising the crystal; and a method for producing the crystal.

BACKGROUND ART

Generally, when a compound is used as an active ingredient of a pharmaceutical product, the chemical stability and physical stability of the compound are necessary to ensure stable quality retention and/or easy storage management. Therefore, a stable-form crystal is the preferable final form of the compound. Generally, the most stable-form crystal is often selected as an active pharmaceutical ingredient of a pharmaceutical product. Further, the guidelines for residual solvents of pharmaceutical products in the ICH (International Conference on Harmonization of Technical Requirements for Registration of Pharmaceuticals for Human Use) guidelines specify the acceptability and acceptable amount of various solvents. Since solvents to be used for the production of pharmaceutical products are often toxic, in view of safety, it is preferable to reduce residual solvents as much as possible during the manufacturing process.

Currently, a plurality of AKT inhibitors usable as antitumor agents has been reported. Patent Document 1 discloses an imidazooxazine compound (chemical name: trans-3-amino-1-methyl-3-(4-(3-phenyl-5H-imidazo[1,2-c]pyrido[3,4-e][1,3]oxazin-2-yl)phenylcyclobutanol (this compound may hereinafter be referred to as "Compound (1)")) represented by Formula (1) below, as a compound having a superior AKT inhibitory action and antitumor activity.

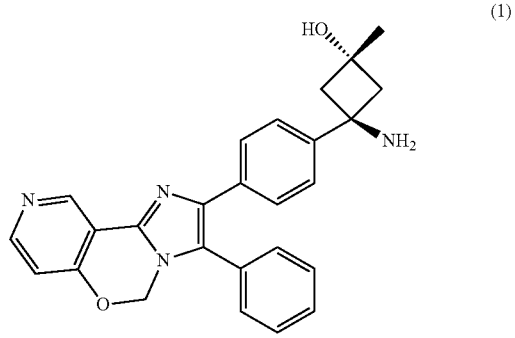 [SMILES: C[C@]1(O)C[C@@](N)(c2ccc(-c3nc4n(c3-c3ccccc3)COc3ccncc3-4)cc2)C1]

(1)

However, the crystal form of this compound is completely unknown, and a method for producing a stable-form crystal of high-purity imidazooxazine compound while ensuring sufficient reproducibility has not been reported at present.

CITATION LIST

Patent Documents

Patent Document 1: WO2012/137870

SUMMARY OF INVENTION

Technical Problem

An object of the present invention is to provide a crystal of Compound (1) useful as an antitumor agent, the crystal having excellent stability, as well as favorable characteristics in tams of its production and formulation into drugs.

Solution to Problem

The inventors of the present invention conducted extensive research to solve the problem; and the inventors discovered crystal II, which is obtained by suspension heating of the imidazooxazine compound represented by Formula (1) in hydrous ethanol. Further, by conducting a method of further suspending crystal II in hot water, the inventors succeeded in obtaining crystal I of Compound (1) having excellent stability and favorable characteristics in terms of its production and formulation into drugs as a pharmaceutical product, and thereby completed the present invention.

More specifically, from the view of the industrial production of a pharmaceutical product, as specified in the ICH guidelines and the like, various qualities including amounts of impurities in the active pharmaceutical ingredient, amounts of residual solvents, and stability of the active pharmaceutical ingredient itself, are required. Accordingly, the present inventors have been considering the final crystal form of Compound (1) to develop the compound as an active pharmaceutical ingredient of a pharmaceutical product. As shown in the Reference Example described later, residual acetonitrile was confirmed by NMR analysis in the crude product of Compound (1) obtained by the production method disclosed in Patent Document 1. Since it is preferable to remove acetonitrile during the production of a pharmaceutical product from the crude product, the residual acetonitrile was removed by conducting suspension heating of the crude product of Compound (1) in hydrous ethanol. However, since crystal II obtained in this step has a characteristic of easily containing ethanol, the residual ethanol in the production may exceed the amount limited by the ICH guidelines. To solve this problem, the inventors subjected the resulting crystal II to suspension in hot water still more, thereby succeeding in obtaining crystal I free of residual solvent. The present inventors thus completed the present invention.

More specifically, the present invention provides the following.

Item 1. A crystal of trans-3-amino-1-methyl-3-(4-(3-phenyl-5H-imidazo[1,2-c]pyrido[3,4-e][1,3]oxazin-2-yl)phenyl)cyclobutanol having at least 5 peaks of diffraction angle (2θ±0.1°) selected from 7.7°, 9.5°, 10.3°, 12.3°, 14.5°, 15.6°, 16.3°, 17.8°, 18.3°, 19.3°, 20.9°, 22.8°, 24.2°, 25.7°, 26.8°, 27.7°, 29.0° and 30.1° in a powder X-ray diffraction spectrum.

Item 2. The crystal according to Item 1, wherein the crystal has peaks of diffraction angle (2θ±0.1°) at 7.7°, 9.5°, 10.3°, 12.3°, 14.5°, 15.6°, 16.3°, 17.8°, 18.3°, 19.3°, 20.9°, 22.8°, 24.2°, 25.7°, 26.8°, 27.7°, 29.0° and 30.1° in a powder X-ray diffraction spectrum.

Item 3. The crystal according to Item 1 or 2, wherein the crystal has an endothermic peak near 230° C. in differential scanning calorimetry (DSC).

Item 4. A pharmaceutical composition comprising the crystal according to any one of Items 1 to 3.

Item 5. A pharmaceutical composition for oral administration, comprising the crystal according to any one of Items 1 to 3.

Item 6. A method for producing the crystal according to any one of Items 1 to 3, comprising the steps of:

(1) subjecting trans-3-amino-1-methyl-3-(4-(3-phenyl-5H-imidazo[1,2-c]pyrido[3,4-e][1,3]oxazin-2-yl)phenyl)cyclobutanol to suspension heating in hydrous ethanol to obtain a suspension;

(2) obtaining a solid of trans-3-amino-1-methyl-3-(4-(3-phenyl-5H-imidazo[1,2-c]pyrido[3,4-e][1,3]oxazin-2-yl)phenyl)cyclobutanol from the suspension obtained in step (1); and (3) subjecting the solid of trans-3-amino-1-methyl-3-(4-(3-phenyl-5H-imidazo[1,2-c]pyrido[3,4-e][1,3]oxazin-2-yl)phenyl)cyclobutanol obtained in step (2) to suspension heating in hot water.

Advantageous Effects of Invention

Since the crystal I of imidazooxazine compound of the present invention has excellent storage stability, it is superior to other crystal forms in terms of, for example, purity, handling (lower hygroscopic property), fluidity, grindability and/or quality control, and the like, and thus, it is useful as a suitable crystal for drug formulation of a pharmaceutical product.

Further, crystal I of the present invention contains a residual solvent in an amount no more than the standard value limited by the guidelines in the ICH for residual solvents in pharmaceutical products, and therefore is safe as a pharmaceutical product.

DESCRIPTION OF EMBODIMENTS

In this specification, the term "Compound (1)" means "trans-3-amino-1-methyl-3-(4-(3-phenyl-5H-imidazo[1,2-c]pyrido[3,4-e][1,3]oxazin-2-yl)phenyl)cyclobutanol", and includes both amorphous and crystal.

In this specification, the terms "crystal" and "amorphous" are interpreted according to general definition.

Due to the characteristic of powder X-ray diffraction itself, the diffraction angle and the entire peak pattern are important in determining the identity of crystals. Since the relative intensity of powder X-ray diffraction pattern varies to some extent depending on the direction of crystal growth, the size of the particles, and measurement conditions, the relative intensity should not be strictly interpreted.

The values obtained from various powder X-ray diffraction patterns may contain errors to some extent depending on the direction of crystal growth, the size of the particles, measurement conditions, and the like. Therefore, in this specification, the values of diffraction angle (2θ) in a powder X-ray diffraction pattern may contain measurement errors in a range of about ±0.1°.

Further, regarding the endothermic peak in a differential scanning calorimeter (DSC) curve, the measurement temperature may vary depending on the temperature increase range per minute, the purity of the sample, and the like. In this specification, the term "near" means a range of ±5.0° C.

Figure 3:
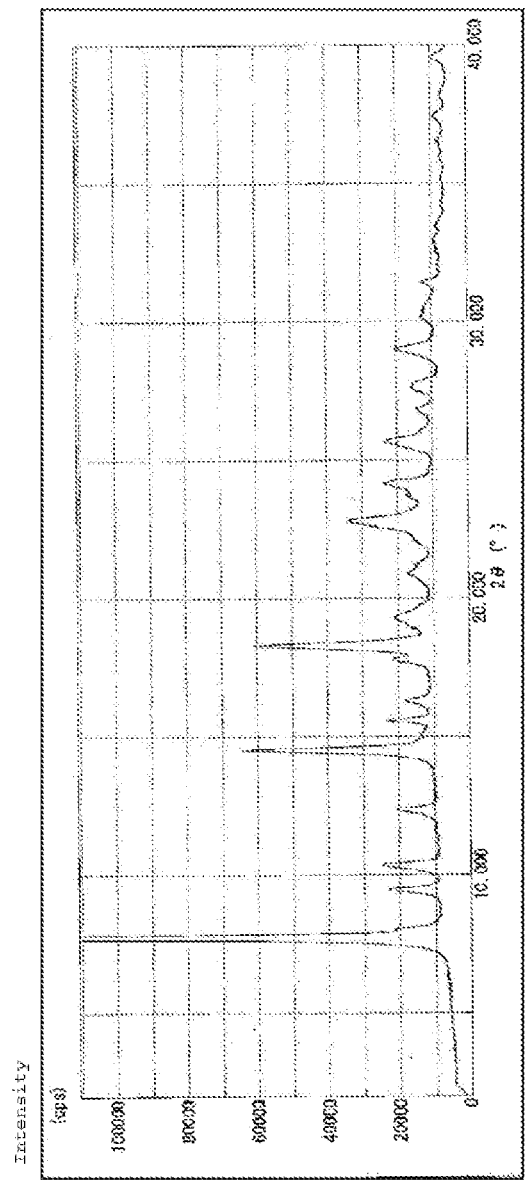
FIG. 3 shows a powder X-ray diffraction spectrum of crystal I of Compound (1) obtained in Example 1 (the vertical axis represents intensity (cps) and the horizontal axis represents diffraction angle (2θ)).
Figure 4:
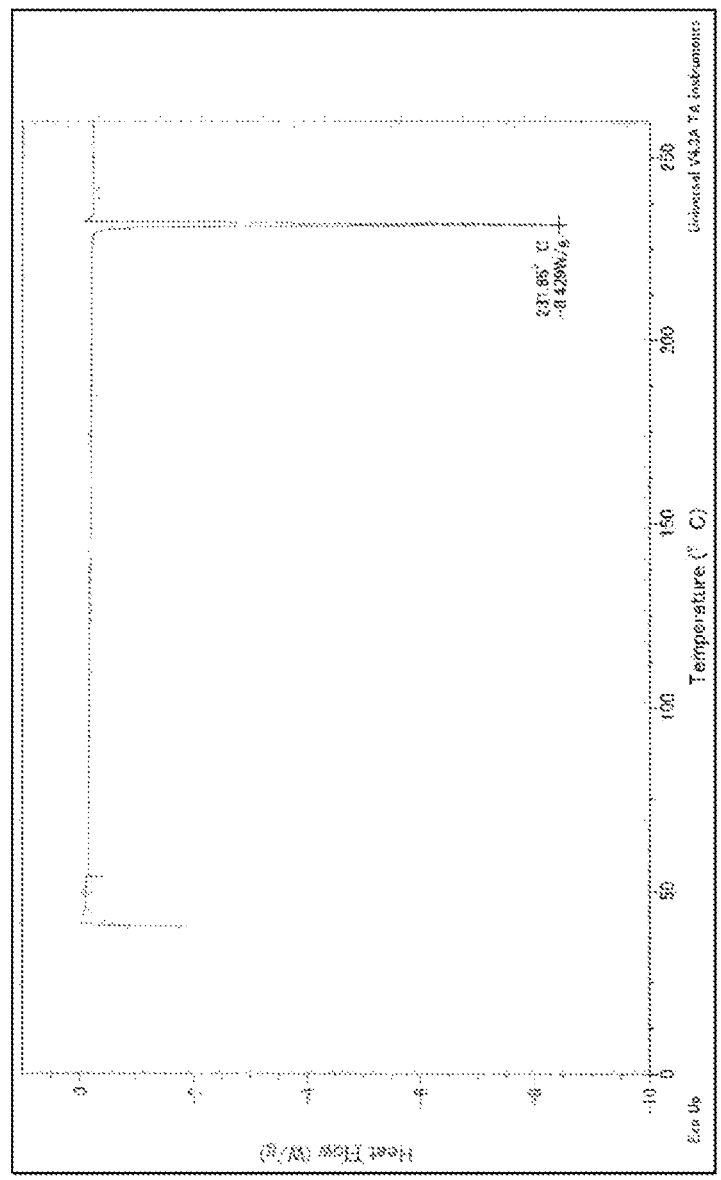
FIG. 4 shows a differential scanning calorimetry (DSC) curve of crystal I of Compound (1) obtained in Example 1.
Figure 5:
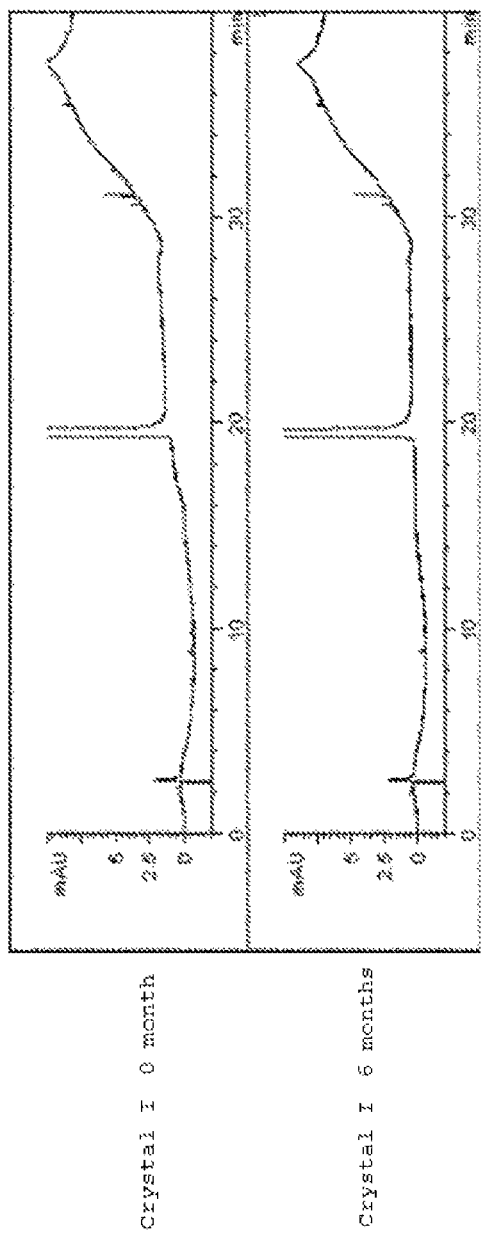
FIG. 5 shows HPLC data that analyzes the increasing amount of analogs in a stability test.

Crystal I of Compound (1) preferably shows the powder X-ray diffraction spectrum shown in FIG. 3 and/or the differential scanning calorimetry (DSC) curve shown in FIG. 4.

The characteristic peaks of diffraction angle (2θ±0.1°) in the powder X-ray diffraction spectrum of crystal I of Compound (1) include 7.7°, 9.5°, 10.3°, 12.3°, 14.5°, 15.6°, 16.3°, 17.8°, 18.3°, 19.3°, 20.9°, 22.8°, 24.2°, 25.7°, 26.8°, 27.7°, 29.0° and 30.1°.

Crystal I of Compound (1) of the present invention is a crystal showing at least 5 peaks, preferably at least 8 peaks, particularly preferably all peaks, of the above peaks.

Further, the endothermic measurement temperature in the differential scanning calorimetry (DSC) curve of crystal I of Compound (1) is near 228° C. to 232° C., preferably near 230° C.

Compound (1) can be synthesized according to the method, such as Reference Example described later. The synthesis method of Compound (1) is, however, not limited to the Reference Example described later.

Crystal I of Compound (1) of the present invention can be produced by a method, such as the method that comprising subjecting the imidazooxazine compound represented by Formula (1) to suspension heating in hydrous ethanol, followed by suspension heating in hot water.

More specifically, Compound (1) is suspended in a mixture of ethanol in an amount of 1 to 100 times, preferably 1 to 50 times, and water in an amount of 1 to 100 times, preferably 1 to 50 times. The mixture is heated under stirring for 1 to 100 hours, preferably 1 to 24 hours, followed by cooling, collection by filtration, and drying, thereby obtaining crystal II. The mixing ratio of the mixture of water and ethanol may be suitably selected; hence the mixing ratio is preferably such that the ratio of water:ethanol (v/v) is 1:0.1 to 10, more preferably 1:0.5 to 2, and particularly preferably 1:1. The heating temperature at this step may be suitably set; hence the heating temperature is preferably 40° C. or more, and more preferably 40 to 60° C.

Subsequently, the resulting crystal II is suspended in water in the amount of 1 to 100 times, preferably 10 to 50 times, and the suspension is heated under reflux for 1 to 120 hours, and preferably 12 to 48 hours, followed by cooling, collection by filtration, and drying, thereby obtaining crystal I as white powder. The heating temperature in this step may be suitably set; hence, the heating temperature is preferably 70° C. or more, and more preferably 70 to 90° C.

To accelerate the crystallization of crystal I, an appropriate amount of crystal I of Compound (1) or a mixed crystal containing crystal I could be added as seed crystal. The amount of the seed crystal to be added is 0.01 to 5 (w/v) %, and preferably 0.03 to 1 (w/v) % based on the solvent amount. Further, crystallization may be performed under stirring so as to shorten the crystallization time and control particle diameter.

In the present invention, the term "cooling" means keeping the temperature of the solution at 40° C. or less, preferably at room temperature or less. The cooling time is preferably 0.5 hours or more, and more preferably 1 hour or more.

The precipitated crystal may be isolated and purified from a solution in which the crystal is dissolved, a mixed solution, or the like, by a known isolation and purification means, such as filtration, washing with water, or drying under reduced pressure.

Crystal I of Compound (1) of the present invention shows excellent solid stability (storage stability, etc.). In the development of a pharmaceutical product, it is important for a candidate compound to show a solid stability in tams of both industrial operation and quality retention. Further, the amount of the residual solvent in crystal I of Compound (1) of the present invention is no more than the amount limited by the ICH guidelines. It is very important that residual solvent is not observed in view of the safety of pharmaceutical products. Therefore, crystal I of Compound (1) of the present invention shows an excellent property as a pharmaceutical product or an active pharmaceutical ingredient of a pharmaceutical product.

The crystal of Compound (1) of the present invention shows excellent AKT inhibitory activity, and is useful as an agent for treating, for example, cancers and tumors. Further, the crystal of Compound (1) of the present invention shows significantly superior selectivity with respect to AKT, and has an advantage in that it shows smaller side effects caused by the inhibition of other kinases.

The crystal of Compound (1) of the present invention shows excellent AKT inhibition activity. In this specification, "AKT" includes human and non-human mammalian AKT, and preferably human AKT. Further, "AKT" includes its isoforms.

Further, with its excellent AKT inhibitory activity, the crystal of Compound (1) of the present invention is useful as an agent for preventing or treating AKT-related diseases, such as cancers.

In using the crystal of Compound (1) of the present invention for an agent for preventing and treating diseases, the crystal can be used in various dosage forms after being pulverized or without being pulverized according to the prevention or treatment purposes. Examples of dosage forms include oral preparations, such as tablets, capsules, granules, fine granules, powdered drugs, or dry syrups; suppositories, inhalation agents, nasal drops, ointments, patches, and injections. Of these, oral preparations are preferable. These pharmaceutical compositions may be produced using a pharmaceutically acceptable carrier by a conventional preparation method known to a person skilled in the art.

As the pharmaceutical carrier, various organic or inorganic carrier materials commonly used as preparation materials may be used as an excipient, binder, disintegrant, lubricant, or colorant in solid preparations; or as a solvent, solubilizing agent, suspending agent, isotonizing agent, buffer, or soothing agent in liquid preparations. Further, a pharmaceutical preparation additive, such as an antiseptic, anti-oxidant, colorant, sweetener, and stabilizer may also be used, if required.

Oral solid preparations can be prepared as follows. An excipient, optionally together with other excipient binder, disintegrant, lubricant, colorant, taste-masking or flavoring agent, etc., is added to the compound of the present invention to produce tablets, coated tablets, granules, powders, capsules, or the like, using an ordinary method.

Examples of excipients include lactose, sucrose, D-mannitol, glucose, starch, calcium carbonate, kaolin, microcrystalline cellulose, and silicic acid anhydride.

Examples of binders include water, ethanol, 1-propanol, 2-propanol, simple syrup, glucose solution, α-starch solution, gelatin solution, D-mannitol, carboxymethyl cellulose, hydroxypropyl cellulose, hydroxypropyl starch, methyl cellulose, ethyl cellulose, shellac, calcium phosphate, and polyvinylpyrrolidone.

Examples of disintegrants include dry starch, sodium alginate, agar powder, sodium hydrogen carbonate, calcium carbonate, sodium lauryl sulfate, stearic acid monoglyceride, and lactose.

Examples of lubricants include purified talc, sodium stearate, magnesium stearate, borax, and polyethylene glycol.

Examples of colorants include titanium oxide and iron oxide.

Examples of taste-masking or flavoring agents include sucrose, wild orange peel, citric acid, and tartaric acid.

Suppositories are prepared as follows. A pharmaceutical carrier known in this field, such as polyethylene glycol, lanolin, cacao butter, and fatty acid triglyceride, is added to the compound of the present invention, optionally together with Tween 80(®) or a like surfactant, followed by production using an ordinary method.

Ointments are prepared as follows. An ordinary base, stabilizer, wetting agent, preservative, and the like, are added as required to the compound of the present invention, and mixed and formulated into drugs using an ordinary method. Examples of bases include liquid paraffin, white petrolatum, white beeswax, octyldodecyl alcohol, and paraffin. Examples of preservatives include methyl parahydroxybenzoate, ethyl parahydroxybenzoate, and propyl parahydroxybenzoate.

Patches can be prepared by coating a general support with the above ointment, cream, gel, paste, or the like, using an ordinary method. Examples of supports include woven or nonwoven fabrics made from cotton, staple fibers, and chemical fibers; and films and foam sheets of soft polyvinyl chloride, polyethylene, polyurethane, and the like.

Injections are prepared as follows. A pH adjuster, buffer, stabilizer, isotonizing agent, topical anesthetic, and the like, are added to the compound of the present invention to produce a subcutaneous injection, an intramuscular injection, or an intravenous injection using an ordinary method. Examples of usable pH adjusters and buffers in this case include sodium citrate, sodium acetate, and sodium phosphate. Examples of usable stabilizers include sodium pyrosulfite, EDTA, thioglycolic acid, and thiolactic acid. Examples of usable topical anesthetics include procaine hydrochloride and lidocaine hydrochloride. Examples of usable isotonizing agents include sodium chloride, glucose, D-mannitol, and glycerin.

The amount of crystal I of Compound (1) to be incorporated in each of such dosage unit forms depends on the conditions of the patient to whom the compound is administered, the dosage form thereof, and the like. However, in general, in the case of an oral agent, the amount of crystal I of Compound (1) is about 0.05 to 1000 mg per dosage unit form. In the case of an injection, the amount of crystal I of Compound (1) is 0.1 to 500 mg per dosage unit form; and in the case of a suppository or external preparation, the amount of crystal I of Compound (1) is about 1 to 1000 mg per dosage unit form.

Further, the daily dose of the medicine in such a dosage form depends on the conditions, body weight, age, gender, and the like, of the patient, and cannot be generalized. However, for example, the daily dose for an adult (body weight: 50 kg) may be generally about 0.05 to 5000 mg, and preferably 0.1 to 1000 mg; and is preferably administered in one dose, or in two to three divided doses, per day.

Further, as described above, crystal I may be obtained, for example, by subjecting the imidazooxazine compound represented by Formula (1) to suspension heating in hydrous ethanol to obtain crystal II, and then suspending crystal II in hot water. Therefore, in the present invention, crystal II of Compound (1) is also useful as an intermediate for producing crystal I. The present invention also thus provides crystal II of Compound (1).

The characteristic peaks of diffraction angle (2θ±0.1°) in the powder X-ray diffraction spectrum of crystal II of Compound (1) include 6.6°, 7.8°, 9.3°, 12.8°, 13.6°, 14.4°, 17.8°, 18.8°, 19.5°, 21.4°, 22.5°, 23.0°, 24.8°, 27.8° and 29.0°.

Crystal II of Compound (1) of the present invention is a crystal having at least 5 peaks, preferably at least 8 peaks, and particularly preferably all peaks, of the above peaks.

EXAMPLES

The present invention is more specifically explained below with reference to Examples; however, the present invention is not limited to these Examples. The present invention is fully described below by way of examples; however, it is understood that various changes and modifications by a person skilled in the art are possible. Therefore, such changes and modifications are included in the present invention as long as they do not depart from the scope of the invention.

In the Examples, commercially available reagents were used, unless otherwise specified. The NMR spectrum was measured by using the AL400 (400 MHz; produced by JEOL). When the deuterated solvent contains tetramethylsilane, tetramethylsilane was used as the internal reference. In other cases, measurement was carried out using peaks of non-deuterated protons remaining in the NMR solvent as the internal reference. All of the δ values are shown by ppm.

Each symbol stands for the following.
s: Singlet
d: Doublet
t: Triplet
dd: Double Doublet
m: Multiplet
brs: Broad Singlet
DMSO-$d_6$: Deuterated dimethyl sulfoxide
CDCl$_3$: Deuterated chloroform
Powder X-Ray Diffraction Measurement Powder X-ray diffraction was performed by lightly pulverizing an appropriate amount of a test substance using an agate mortar as necessary, and measuring the test substance in accordance with the following test conditions.
Device: MiniFlex II, Rigaku Corporation
Target: Cu
X-ray output power: 15 mA, 30 kV
Scanning range: 2.0 to 40.0°
Step size: 0.010°
Scanning speed: 5.00° C./min.
Divergence slit: 1.25°
Scatter slit: open
Receiving slit: open Handling of the device, including data processing, was performed in accordance with the method and procedures specified for each device.

The values obtained from various spectra may vary to some extent depending on the direction of crystal growth, the size of the particles, measurement conditions, and the like. Therefore, the values should not be strictly interpreted.
Thermal Analysis Measurement (Differential Scanning Calorimetry (DSC Measurement))

DSC measurement was performed in accordance with the following test conditions.
Device: TA Instruments Q1000
Sample: about 1 mg
Sample container: aluminum container
Temperature increase rate: increased at 5° C./min to 250° C.
Atmospheric gas: nitrogen
Nitrogen gas flow rate: 50 mL/min Handling of the device, including data processing, was performed in accordance with the method and procedures specified for each device.

Reference Example 1: Synthesis of trans-3-amino-1-methyl-3-(4-(3-phenyl-5H-imidazo[1,2-c]pyrido[3,4-e][1,3]oxazin-2-yl)phenylcyclobutanol (Compound (1))

tert-butyl(trans-3-hydroxy-3-methyl-1-(4-(3-phenyl-5H-imidazo[1,2-c]pyrido[3,4-e][1,3]oxazin-2-yl)phenyl)cyclobutyl)carbamate (27.3 g) synthesized in accordance with the method disclosed in WO2012/137870 was suspended in acetonitrile (550 mL), and methanesulfonic acid (22 mL) was added at room temperature. After stirring for an hour at room temperature, 1M sodium hydroxide aqueous solution (340 mL) was added to quench the reaction. Since the reaction mixture was separated to two layers, water (340 mL) was added to obtain a homogeneous solution. 830 mL of the solvent was distilled off under reduced pressure at 55° C. After returning it to room temperature, the generated solid was collected by filtration. The solid collected by filtration was washed with water, and dried at 70° C., thereby giving a crude product (16.7 g) of the title compound (Compound (1)) as a pale yellow solid.

$^1$H-NMR (CDCl$_3$): δ 9.26 (1H, s), 8.49 (1H, d, J=5.6 Hz), 7.57-7.52 (2H, m), 7.52-7.43 (3H, m), 7.39-7.32 (2H, m), 7.28-7.21 (2H, m), 6.99 (1H, dd, J=5.6, 0.5 Hz), 5.76 (2H, s), 2.65-2.57 (2H, m), 2.39-2.31 (2H, m), 1.64 (3H, s).
Residual Acetonitrile Peak: δ 2.01 (3H, s)
The residual acetonitrile amount calculated from the NMR peak area was about 600 ppm.

Example 1: Production of crystal II of trans-3-amino-1-methyl-3-(4-(3-phenyl-5H-imidazo[1,2-c]pyrido[3,4-e][1,3]oxazin-2-yl)phenylcyclobutanol (Compound (1))

The crude product (480 mg) of Compound (1) obtained in Reference Example 1 was suspended in a mixed solvent of ethanol (2 mL) and water (2 mL). The suspension was stirred at 50° C. for 3 hours, and then cooled to room temperature. The solid was collected by filtration, washed with water, and dried at 40° C., thereby giving crystal II (438 mg) of the title compound as a white solid.

$^1$H-NMR (DMSO-$d_6$): δ 9.01 (1H, d, J=0.5 Hz), 8.48 (1H, d, J=5.4 Hz), 7.56-7.46 (3H, m), 7.45-7.37 (4H, m), 7.32-

7.28 (2H, m), 7.21 (1H, dd, J=5.4, 0.5 Hz), 5.93 (2H, s), 4.74 (1H, s), 3.32 (1H, s), 2.39-2.28 (2H, m), 2.18-2.07 (2H, m), 1.95 (2H, brs), 1.49 (3H, s).
Residual ethanol peak: δ 4.34 (1H, m), 3.43 (2H, m), 1.04 (3H, t, J=7.3 Hz)
The residual ethanol amount calculated from the NMR peak area was about 14000 ppm.

Figure 1:
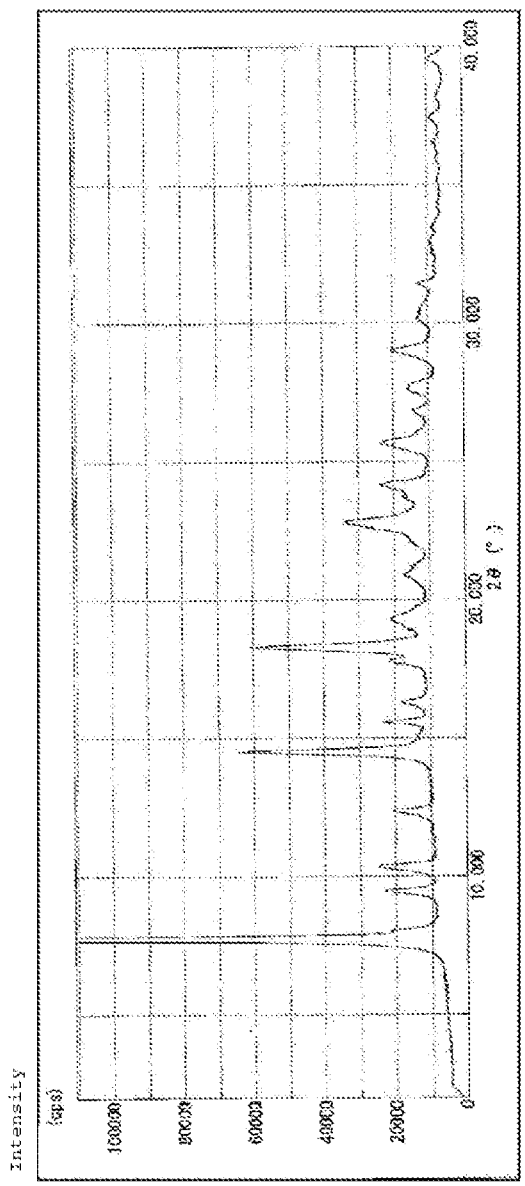
FIG. 1 shows a powder X-ray diffraction spectrum of crystal II of Compound (1) obtained in Example 1 (the vertical axis represents intensity (cps) and the horizontal axis represents diffraction angle (2θ)).

FIG. 1 shows a powder X-ray diffraction spectrum. Characteristic diffraction angles (2θ±0.1°): 6.6°, 7.8°, 9.3°, 12.8°, 13.6°, 14.4°, 17.8°, 18.8°, 19.5°, 21.4°, 22.5°, 23.0°, 24.8°, 27.8° and 29.0°.

Figure 2:
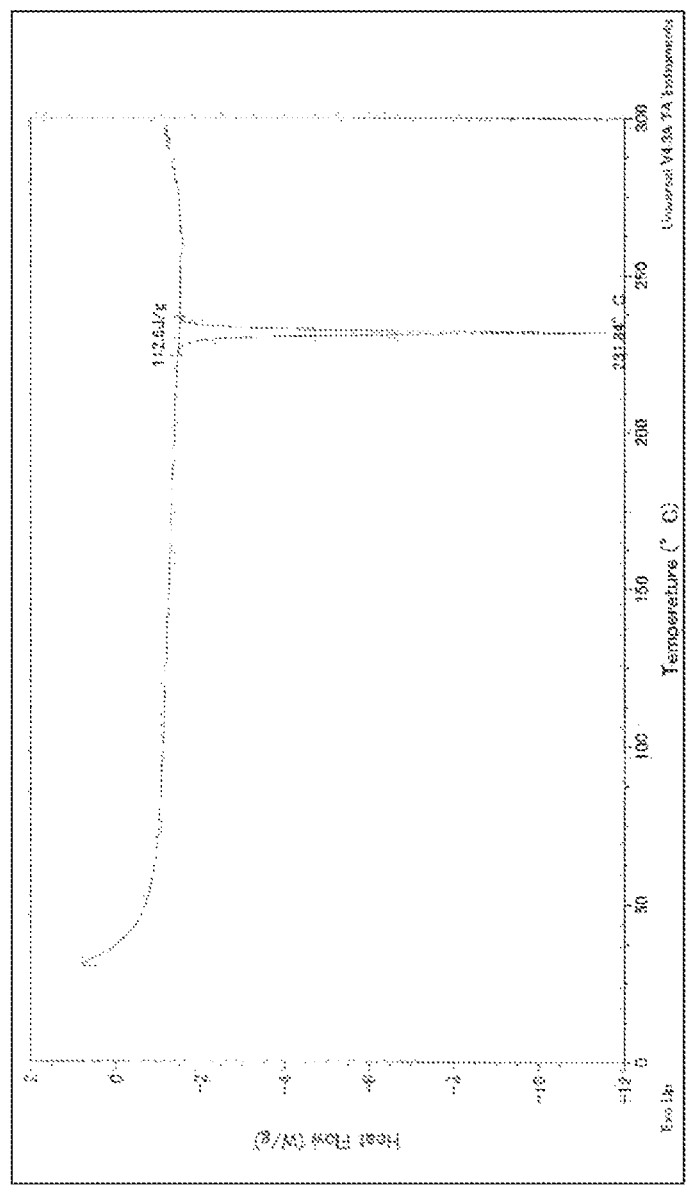
FIG. 2 shows a differential scanning calorimetry (DSC) curve of crystal II of Compound (1) obtained in Example 1.

FIG. 2 shows a differential scanning calorimetry (DSC) curve.

Endothermic peak in the differential scanning calorimetry (DSC) curve: near 228° C. to 232° C.

Production of crystal I of trans-3-amino-1-methyl-3-(4-(3-phenyl-5H-imidazo[1,2-c]pyrido[3,4-e][1,3]oxazin-2-yl)phenylcyclobutanol (Compound (1))

Crystal II (16.16 g) obtained above was suspended in water (160 mL) and stirred for 31 hours while heating at 80° C., and then cooled to room temperature. The solid was collected by filtration, washed with water, and dried at 80° C., thereby giving crystal I (15.98 g) of the title compound as a white solid.
$^1$H-NMR (CDCl$_3$): δ 9.26 (1H, s), 8.49 (1H, d, J=5.6 Hz), 7.57-7.52 (2H, m), 7.52-7.43 (3H, m), 7.39-7.32 (2H, m), 7.28-7.21 (2H, m), 6.99 (1H, dd, J=5.6, 0.5 Hz), 5.76 (2H, s), 2.65-2.57 (2H, m), 2.39-2.31 (2H, m), 1.64 (3H, s).
A residual solvent peak was not observed.

FIG. 3 shows a powder X-ray diffraction spectrum. Characteristic diffraction angles (2θ±0.1°): 7.7°, 9.5°, 10.3°, 12.3°, 14.5°, 15.6°, 16.3°, 17.8°, 18.3°, 19.3°, 20.9°, 22.8°, 24.2°, 25.7°, 26.8°, 27.7°, 29.0° and 30.1°.

FIG. 4 shows a differential scanning calorimetry (DSC) curve.

Endothermic peak in the differential scanning calorimetry (DSC) curve: near 228° C. to 232° C.

Example 2: Solid Stability Test

The storage stability of crystal I of the imidazooxazine compound obtained in accordance with Example 1 was tested after six months of storage at 40° C.
Storage condition: 40° C. (hermetically sealed)
Measurement point: Six months
Amount: About 30 mg
Container: Brown glass bottle
The powder X-ray diffraction of the sample after storage was measured using the method described above. Alternations in analog amount were analyzed by HPLC according to the following manner.
Method for preparing a sample solution: the sample was dissolved in 50% acetonitrile so that the concentration of the sample became 0.5 mg/mL.
Column: Acentis express C18, 4.6×150 mm, 2.7 μm,
Column temperature: 40° C.
Column flow rate: 1.5 mL/min
Mobile phase: A; 0.1% phosphate, B; acetonitrile
Detection UV: 210 nm
Gradient:

| Time (min) | A | B |
| --- | --- | --- |
| 0 to 4 | 95%→70% | 5%→30% |
| 4 to 7 | 70%→10% | 30%→90% |
| 7 to 8 | 10% | 90% |

The results revealed that changes in powder X-ray diffraction pattern were not observed in crystal I, and that, therefore, crystal I was a very stable crystal. Further, crystal I contained only a small amount of analogs, and the amount of the analogs was not increased after six months of storage at 40° C.

The invention claimed is:

1. A crystal of trans-3-amino-1-methyl-3-(4-(3-phenyl-5H-imidazo[1,2-c]pyrido[3,4-e][1,3]oxazin-2-yl)phenyl)cyclobutanol having at least 5 of diffraction angle (2θ±0.1°) selected from 7.7°, 9.5°, 10.3°, 12.3°, 14.5°, 15.6°, 16.3°, 17.8°, 18.3°, 19.3°, 20.9°, 22.8°, 24.2°, 25.7°, 26.8°, 27.7°, 29.0° and 30.1° in a powder X-ray diffraction spectrum.

2. The crystal according to claim 1, wherein the crystal has peaks of diffraction angle (2θ±0.1°) at 7.7°, 9.5°, 10.3°, 12.3°, 14.5°, 15.6°, 16.3°, 17.8°, 18.3°, 19.3°, 20.9°, 22.8°, 24.2°, 25.7°, 26.8°, 27.7°, 29.0° and 30.1° in a powder X-ray diffraction spectrum.

3. The crystal according to claim 1, wherein the crystal has an endothermic peak near 230° C. in differential scanning calorimetry (DSC).

4. A pharmaceutical composition comprising the crystal according to claim 1.

5. A pharmaceutical composition for oral administration, comprising the crystal according to claim 1.

6. A method for producing the crystal according to claim 1, comprising the steps of:
(1) subjecting trans-3-amino-1-methyl-3-(4-(3-phenyl-5H-imidazo[1,2-c]pyrido[3,4-e][1,3]oxazin-2-yl)phenyl)cyclobutanol to suspension heating in hydrous ethanol to obtain a suspension;
(2) obtaining a solid of trans-3-amino-1-methyl-3-(4-(3-phenyl-5H-imidazo[1,2-c]pyrido[3,4-e][1,3]oxazin-2-yl)phenyl)cyclobutanol from the suspension obtained in step (1); and
(3) subjecting the solid of trans-3-amino-1-methyl-3-(4-(3-phenyl-5H-imidazo[1,2-c]pyrido[3,4-e][1,3]oxazin-2-yl)phenyl)cyclobutanol obtained in step (2) to suspension heating in hot water.

* * * * *